(12) United States Patent
Burk

(10) Patent No.: US 7,932,420 B2
(45) Date of Patent: Apr. 26, 2011

(54) SULFONAMIDES

(75) Inventor: Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 36 days.

(21) Appl. No.: 11/986,344

(22) Filed: Mar. 14, 2008

(65) Prior Publication Data
US 2008/0167331 A1   Jul. 10, 2008

Related U.S. Application Data

(63) Continuation of application No. 11/426,482, filed on Jun. 26, 2006, now Pat. No. 7,314,890.

(60) Provisional application No. 60/710,719, filed on Aug. 22, 2005.

(51) Int. Cl.
C07C 61/06 (2006.01)
(52) U.S. Cl. ........ 562/503; 562/444; 562/506; 514/646; 514/659
(58) Field of Classification Search .................. 514/646, 514/659; 562/444, 503, 506
See application file for complete search history.

(56) References Cited

U.S. PATENT DOCUMENTS

| | | | |
|---|---|---|---|
| 6,344,485 B1 * | 2/2002 | Cameron et al. | 514/601 |
| 7,314,890 B2 * | 1/2008 | Burk | 514/646 |

OTHER PUBLICATIONS

WoldeMussie et al., "Neuroprotection of Retinal Ganglion Cells by Brimonidine in Rates with Laser-Induced Chronic Ocular Hypertension", Investigative Ophthalmology & Visual Science, Nov. 2001, vol. 42, No. 12.*
Weinreb et. al., "Is Neuroprotection a Viable Therapy for Glaucoma?" Arc Opthamalol, vol. 117, Nov. 1999.*
Bito, L.Z. *Biological Protection with Prostaglandins* Cohen, M.M., ed., Boca Raton, Fla, CRC Press Inc., 1985, pp. 231-252.
Bito, L. Z., *Applied Pharmacology in the Medical Treatment of Glaucomas* Drance, S. M. and Neufeld, A. H. eds., New York, Grune & Stratton, 1984, pp. 477-505.
Cioffi and Van Buskirk [*Surv. Of Ophthalmol.*, 38, Suppl. P. S107-16, discussion S116-117, May 1994] in the article, "Microvasculature of the Anterior Optic Nerve".
Jones et. al., "11, 12-Secoprostaglandins. 4. 7-(N-Alkylmethanesulfonamido)heptanoic Acids", Journal of Medicinal Chemistry, 1977, vol. 20, No. 10, pp. 1299-1304.
Matsui published a paper on the "Ophthalmologic aspects of Systemic Vasculitis" [*Nippon Rinsho*, 52 (8), p. 2158-2163, Aug. 1994].
Schwartz, in "Circulatory Defects of the Optic Disk and Retina in Ocular Hypertension and High Pressure Open-Angle Glaucoma" [*Surv. Ophthalmol.*, 38, Suppl. pp. S23-24, May 1994].
Starr, M.S. Exp. Eye Res. 1971, 11, pp. 170-177.

* cited by examiner

*Primary Examiner* — Janet L Andres
*Assistant Examiner* — Heidi Reese
(74) *Attorney, Agent, or Firm* — Kevin J. Forrestal; John E. Wurst; Doina G. Ene

(57) ABSTRACT

The present invention provides

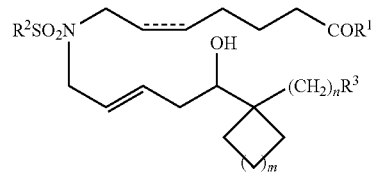

wherein $R^1$ is selected from the group consisting of $C_1$-$C_{10}$ alkoxy, OH and $NR^4R^5$;
$R^2$ is selected from the group consisting of $C_1$-$C_{10}$ alkyl and $(CH_2)_n OH$;
$R^3$ is selected from the group consisting of $C_1$-$C_{10}$ alkyl, heteroaryl, e.g. thienyl, furanyl and pyridyl, phenyl, mono-, -di-, tri-substituted phenyl and heteroaryl;
$R^4$ and $R^5$ are independently selected from the group consisting of H, $C_1$-$C_{10}$ alkyl, $C_1$-$C_{10}$ alkyl hydroxyl;
m is 0 or an integer from 1 to 3 and
n is an integer of from 1 to 4.
These compounds are useful in lowering intraocular pressure and/or treating glaucoma or providing neuroprotection to the eye of a human patient.

13 Claims, 2 Drawing Sheets

SCHEME 2**

SULFONAMIDES

CROSS REFERENCE TO RELATED APPLICATIONS

This application is a continuation of U.S. patent application Ser. No. 11/426,482, which was filed on Jun. 26, 2006, now U.S. Pat. No. 7,314,890 and is based on U.S. Provisional Application No. 60/710,719, which was filed on Aug. 22, 2005, and both of which applications are hereby incorporated by reference.

BACKGROUND OF THE INVENTION

1. Field of the Invention

The present invention relates to novel sulfonamide compounds which are useful in lowering intraocular pressure and/or treating glaucoma or may be used in providing neuroprotection to the eye of a human.

2. Description of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical α-adrenoreceptor antagonists have traditionally been the drugs of choice for treating glaucoma.

It has long been know that one of the sequelae of glaucoma is damage to the optic nerve head. This damage, referred to as "cupping", results in depressions in areas of the nerve fiber of the optic disk. Loss of sight from this cupping is progressive and can lead to blindness if the condition is not treated effectively.

Unfortunately lowering intraocular pressure by administration of drugs or by surgery to facilitate outflow of the aqueous humor is not always effective in obviating damage to the nerves in glaucomatous conditions. This apparent contradiction is addressed by Cioffi and Van Buskirk [*Surv. of Opthalmol.,* 38, Suppl. p. S107-16, discussion S116-17, May 1994] in the article, "Microvasculature of the Anterior Optic Nerve". The abstract states:

> The traditional definition of glaucoma as a disorder of increased intraocular pressure (IOP) oversimplifies the clinical situation. Some glaucoma patients never have higher than normal IOP and others continue to develop optic nerve damage despite maximal lowering of IOP. Another possible factor in the etiology of glaucoma may be regulation of the regional microvasculature of the anterior optic nerve. One reason to believe that microvascular factors are important is that many microvascular diseases are associated with glaucomatous optic neuropathy.

Subsequent to Cioffi, et al., Matusi published a paper on the "Opthalmologic aspects of Systemic Vasculitis" [*Nippon Rinsho,* 52 (8), p. 2158-63, August 1994] and added further support to the assertion that many microvascular diseases are associated with glaucomatous optic neuropathy. The summary states:

> Ocular findings of systemic vasculitis, such as polyarteritis nodosa, giant cell angitis and aortitis syndrome were reviewed. Systemic lupus erythematosus is not categorized as systemic vasculitis, however its ocular findings are microangiopathic. Therefore, review of its ocular findings was included in this paper. The most common fundus finding in these diseases is ischemic optic neuropathy or retinal vascular occlusions. Therefore several points in diagnosis or pathogenesis of optic neuropathy and retinal and choroidal vaso-occlusion were discussed. Choroidal ischemia has come to be able to be diagnosed clinically, since fluorescein angiography was applied in these lesions. When choroidal arteries are occluded, overlying retinal pigment epithelium is damaged. This causes disruption of barrier function of the epithelium and allows fluid from choroidal vasculatures to pass into subsensory retinal spaces. This is a pathogenesis of serous detachment of the retina. The retinal arterial occlusion formed non-perfused retina. Such hypoxic retina released angiogenesis factors which stimulate retinal and iris neovascularizations and iris neovascularizations may cause neovascular glaucoma.

B. Schwartz, in "Circulatory Defects of the Optic Disk and Retina in Ocular Hypertension and High Pressure Open-Angle Glaucoma" [*Surv. Ophthalmol.,* 38, Suppl. pp. S23-24, May 1994] discusses the measurement of progressive defects in the optic nerve and retina associated with the progression of glaucoma. He states:

> Fluorescein defects are significantly correlated with visual field loss and retinal nerve fiber layer loss. The second circulatory defect is a decrease of flow of fluorescein in the retinal vessels, especially the retinal veins, so that the greater the age, diastolic blood pressure, ocular pressure and visual field loss, the less the flow. Both the optic disk and retinal circulation defects occur in untreated ocular hypertensive eyes. These observations indicate that circulatory defects in the optic disk and retina occur in ocular hypertension and open-angle glaucoma and increase with the progression of the disease.

Thus, it is evident that there is an unmet need for agents that have neuroprotective effects in the eye that can stop or retard the progressive damage that occurs to the nerves as a result of glaucoma or other ocular afflictions.

> Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.*

1971, 11, pp. 170-177; Bito, L. Z. *Biological Protection with Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

BRIEF SUMMARY OF THE INVENTION

The present invention provides compounds represented by the formula:

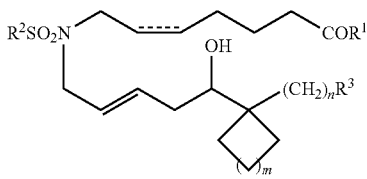

wherein $R^1$ is selected from the group consisting of $C_1$-$C_{10}$ alkoxy, OH and $NR^4R^5$;
$R^2$ is selected from the group consisting of $C_1$-$C_{10}$ alkyl and $(CH_2)_nOH$;
$R^3$ is selected from the group consisting of $C_1$-$C_{10}$ alkyl, heteroaryl, e.g. thienyl, furanyl and pyridyl, phenyl, mono-, -di-, tri-substituted phenyl and heteroaryl;
$R^4$ and $R^5$ are independently selected from the group consisting of H, $C_1$-$C_{10}$ alkyl, $C_1$-$C_{10}$ alkyl hydroxyl;
m is 0 or an integer from 1 to 3 and
n is an integer of from 1 to 4.
These compounds may be used in lowering intraocular pressure and/or treating glaucoma or may be used in providing neuroprotection to the eye of a human.

DETAILED DESCRIPTION OF THE INVENTION

Figure 1:
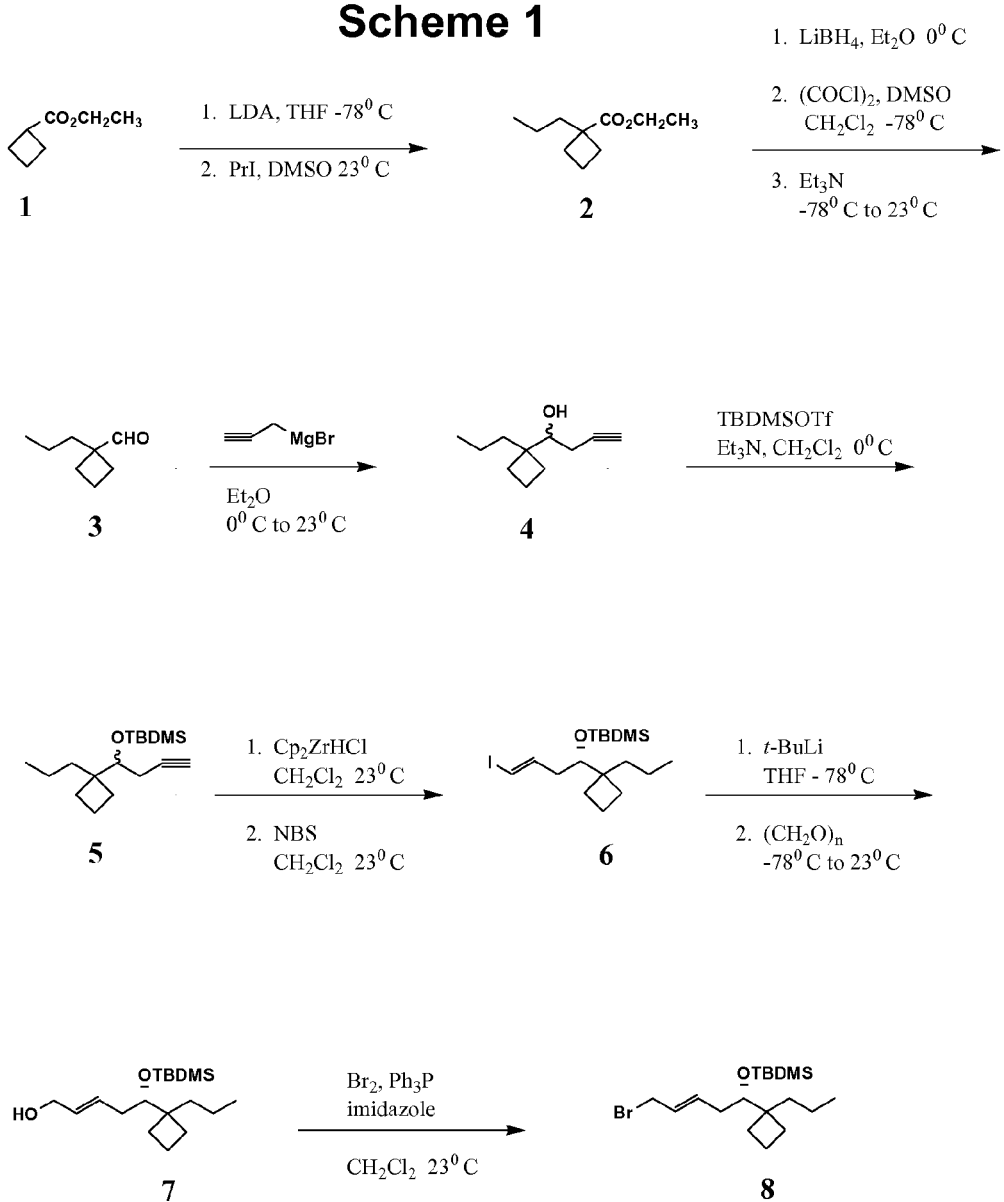
FIG. 1 describes a general synthetic scheme for the preparation of certain intermediates useful in the preparation of the compounds of the invention.
Figure 2:
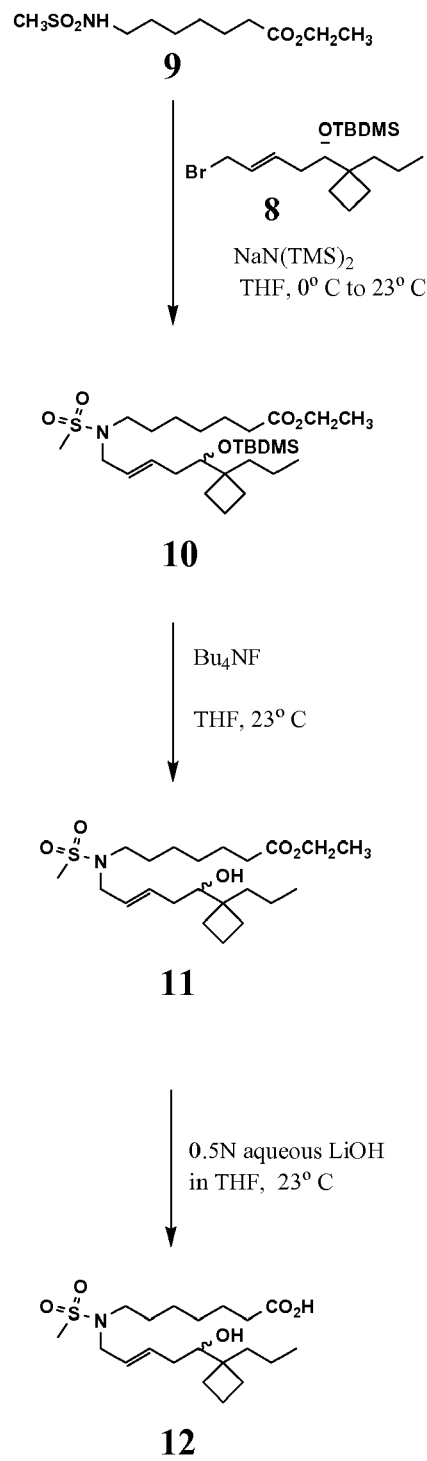
FIG. 2 describes a general synthetic scheme for the preparation of certain of the compounds of the invention.

The novel compounds of the present invention have the general formula

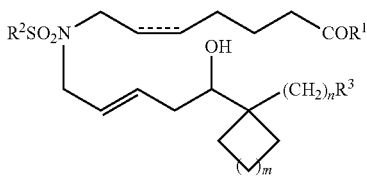

wherein $R^1$ is selected from the group consisting of $C_1$-$C_{10}$ alkoxy, OH and $NR^4R^5$;
$R^2$ is selected from the group consisting of $C_1$-$C_{10}$ alkyl and $(CH_2)_nOH$;
$R^3$ is selected from the group consisting of $C_1$-$C_{10}$ alkyl, heteroaryl, e.g. thienyl, furanyl and pyridyl, phenyl, mono-, -di-, tri-substituted phenyl and heteroaryl;
$R^4$ and $R^5$ are independently selected from the group consisting of H, $C_1$-$C_{10}$ alkyl, $C_1$-$C_{10}$ alkyl hydroxyl;
m is 0 or an integer from 1 to 3 and
n is an integer of from 1 to 4.

Preferably $R^1$ is OH or O-lower alkyl or $N(H)_p$(lower alkyl)$_q$ or $N(H)_p$ (lower alkyl hydroxyl)$_q$ wherein p is 0 or 1 and q is 1 or 2. Lower alkyl is defined as a $C_1$ to $C_6$ alkyl.

More preferably $R^1$ is OH or $OCH_3$.

Preferably the n associated with $R^2$ is 1 and $R^2$ is lower alkyl.

$R^3$ is preferably selected from the group consisting of phenyl, furanyl and thienyl.

Finally, preferably the benzylic OH group is oriented as an α OH group.

Specific compounds of the invention include:
7-[[5-Hydroxy-5-(1-propylcyclobutyl)pent-2-enyl]methanesulfonylamino]heptanoic acid ethyl ester (11).
7-[[5-Hydroxy-5-(1-propylcyclobutyl)pent-2-enyl]methanesulfonylamino]heptanoic acid (12).

The compounds of the invention are especially useful in treating ocular hypertension, i.e. lowering elevated intraocular pressure (IOP), and/or glaucoma. These compounds are useful in providing neuroprotection to the eye of a human.

Pharmaceutical compositions including the compounds of this invention may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjuster | 0-10 |
| buffer | 0.01-10 |
| pH adjuster | q.s. pH 4.5-8.0 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations for use in the method of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 μl.

The invention is further illustrated by the following examples which are illustrative of a specific mode of practicing the invention and are not intended as limiting the scope of the claims. In the examples, the numbers of the compounds correspond to the numbers in the Figures.

Example 1

1-Propylcyclobutanecarboxylic acid ethyl ester (2)

Ethyl cyclobutanecarboxylate 1 (25.0 g, 0.195 mol) was added to a solution of lithium diisopropylamide (97.5 mL of a 2.0M solution in THF, 0.195 mol) in THF (200 mL) at −78° C. After 30 min the reaction solution was warmed to room temperature and transferred via cannula to a solution of 1-iodopropane (49.7 g, 0.293 mol) in DMSO (104 mL) while maintaining the temperature between 15-20° C. After stirring for an additional 30 min the precipitated salts were removed by vacuum filtration. The filtrate was concentrated in vacuo, diluted with hexane and washed with 1 N HCl, saturated aqueous NaHCO$_3$ and brine. The organic portion was dried (MgSO$_4$), filtered and concentrated in vacuo. The residue was purified by vacuum distillation (105-108° C., 20-30 mmHg) to give 16 g (48%) of the ester 2 as a clear, colorless oil.

Example 2

1-Propylcyclobutanecarboxaldehyde (3)

Lithium borohydride (4.0 g, 0.186 mol) was added to a solution of the ester 2 (16.0 g, 0.093 mol) in Et$_2$O (200 mL) at 0° C. The reaction was allowed to warm to room temperature and stirred for 16 h. The reaction was quenched by careful addition of 1N NaOH and extracted with Et$_2$O. The organic portion was washed with brine, dried (MgSO$_4$), filtered and concentrated in vacuo to yield the corresponding alcohol as a clear, colorless oil.

Dimethylsulfoxide (28.4 mL, 0.4 mol) was added dropwise to a stirred solution of oxalyl chloride (100 mL of a 2.0M solution in CH$_2$Cl$_2$, 0.20 mol) in CH$_2$Cl$_2$ (300 mL) at −78° C. After 15 min a solution of the alcohol (prepared above) in CH$_2$Cl$_2$ (100 mL) was added and the reaction was stirred for 1 h. Triethylamine (123 mL, 0.88 mol) was added and the reaction was allowed to warm to room temperature. Saturated aqueous NaHCO$_3$ was added and the organic portion was separated. The organic portion was then washed with brine, dried (MgSO$_4$), filtered and concentrated in vacuo. FCC (silica gel, 9:1 pentane:CHCl$_3$) afforded 6.85 g (67%) of the aldehyde 3 as a clear, colorless oil.

Example 3

1-(1-Propylcyclobutyl)but-3-yn-1-ol (4)

Propargyl bromide (0.27 mL, 2.4 mmol) was added to a mixture of magnesium (1.1 g, 45 mmol) and mercuric chloride (30 mg, 0.117 mmol) in Et$_2$O (60 mL). The mixture was warmed to 40° C. until bubbling commenced. The remainder of the propargyl bromide (2.1 mL, 19 mmol) was added in small portions. After ~1.5 h the reaction became cloudy white. A solution of the aldehyde 3 (0.8 g, 7 mmol) in Et$_2$O (4 mL) was added and the reaction was stirred for 16 h. The reaction was then quenched by cautiously adding saturated aqueous NH$_4$Cl. The resultant mixture was extracted with Et$_2$O. The organic portion was washed with brine, dried (MgSO$_4$), filtered and concentrated in vacuo. FCC (silica gel, 1:1 pentane/CH$_2$Cl$_2$) gave 1.0 g (94%) of the alcohol 4.

Example 4 tert-Butyldimethyl-[1-(1-propylcyclobutyl)but-3-ynyloxy]silane (5)

t-Butyldimethylsilyltrifluoromethanesulfonate (1.8 mL, 7.88 mmol) was added to a solution of triethylamine (2.2 mL, 15.8 mmol) and alcohol 4 (650 mg, 3.94 mmol) in CH$_2$Cl$_2$ (5.0 mL) at 0° C. The reaction was stirred for 1 h and then saturated aqueous NaHCO$_3$ was added. The mixture was extracted with CH$_2$Cl$_2$. The organic portion was washed with brine, dried (Na$_2$SO$_4$), filtered and concentrated in vacuo. FCC (silica gel, 100% hexane) gave 1.7 g (100%) of the silyl ether 5 as a clear, colorless oil.

Example 5 tert-Butyl-[4-iodo-1-(propylcyclobutyl)but-3-enyloxy]dimethylsilane (6)

Bis(cyclopentadienyl)zirconiumchloride hydride (3.1 g, 12.0 mmol) was added to a solution of alkyne 5 (1.7 g, 3.94 mmol) in CH$_2$Cl$_2$ (20 mL) at 23° C. After 0.5 h N-iodosuccinimide (2.6 g, 12.0 mmol) was added. The reaction was stirred for 0.5 h, concentrated in vacuo and the residue was diluted with pentane and washed with saturated aqueous sodium bisulfite. The organic portion was dried (Na$_2$SO$_4$), filtered and concentrated in vacuo. Purification of the residue by FCC (silica gel, 100% pentane) gave 1.2 g (71%) of the vinyl iodide 6 as a clear, light yellow oil.

Example 6

5-(tert-butyldimethylsilanyloxy)-5-(1-propylcyclobutyl)pent-2-en-1-ol (7)

tert-Butyllithium (1.32 mL of a 1.7M solution in pentane, 2.25 mmol) was added to a solution of the vinyl iodide 6 (460 mg, 1.25 mmol) in THF (2.2 mL) at −78° C. After 0.5 h paraformaldehyde (50 mg, 1.67 mmol) was added. The reaction was warmed to room temperature and stirred for 16 h. The reaction was quenched with saturated aqueous $NH_4Cl$ and extracted with EtOAc. The organic portion was dried ($MgSO_4$), filtered and concentrated in vacuo. FCC (silica gel, 4:1 hex/EtOAc) yielded 103 mg (33%) of the alcohol 7 as a clear, colorless oil.

Example 7

[5-Bromo-1-(1-propylcyclobutyl)pent-3-enyloxy] tert-butyldimethylsilane (8)

Bromine (0.17 mL, 3.22 mmol) was added to a solution of triphenylphosphine (844 mg, 3.22 mmol) and imidazole (219 mg, 3.22 mmol) in $CH_2Cl_2$ (11.0 mL) at 23° C. After 0.5 h a solution of the alcohol 7 (838 mg, 2.68 mmol) in $CH_2Cl_2$ (2.7 mL) was added. The reaction was stirred for 1 h, diluted with hexane and then filtered through celite. The filtrate was concentrated in vacuo and purified by FCC (silica gel, 100% hex) to give 870 mg (86%) of the bromide 8 as a clear, light yellow oil.

Example 8

7-[[5-((tert-Butyldimethylsilanyloxy)-5-(1-propylcyclobutyl)pent-2-enyl]methanesulfonylamino]heptanoic acid ethyl ester (10)

Sodium bis(trimethylsilyl)amide (1.1 mL of a 1.0M solution in THF, 1.1 mmol) was added to a solution of the sulfonamide 9 (234 mg, 1.07 mmol) in THF (2.2 mL) at 0° C. The reaction was warmed to room temperature and a solution of the bromide 8 (200 mg, 0.533 mmol) in THF (2.0 mL) was added. The reaction was stirred at room temperature for 16 h, quenched with saturated aqueous $NH_4Cl$ and extracted with EtOAc. The organic portion was washed with brine, dried ($MgSO_4$), filtered and concentrated in vacuo. FCC (silica gel, 6:1 hex/EtOAc) gave 140.7 mg (55%) of the silyl ether 10 as a light yellow viscous oil.

Example 9

7-[[5-Hydroxy-5-(1-propylcyclobutyl)pent-2-enyl] methanesulfonylamino]heptanoic acid ethyl ester (11)

Tetrabutylammonium fluoride (0.58 mL of a 1.0M solution in THF, 0.58 mmol) was added to a solution of the silylether 10 (140.7 mg, 0.29 mmol) in THF (4.5 mL) at 23° C. The reaction was stirred for 16 h, diluted with EtOAc and washed with water. The organic portion was washed with brine, dried ($MgSO_4$), filtered and concentrated in vacuo. FCC (silica gel, 1:1 hex/EtOAc) afforded 97.8 mg (91%) of the alcohol 11 as a light yellow, viscous oil.

Example 10

7-[[5-Hydroxy-5-(1-propylcyclobutyl)pent-2-enyl] methanesulfonylamino]heptanoic acid (12)

Lithium hydroxide (0.50 mL of a 0.5N solution in $H_2O$, 0.122 mmol) was added to a solution of the ester 11 (45 mg, 0.122 mmol) in THF (1.0 mL) at 23° C. The reaction mixture was stirred for 16 h, acidified with 1 N HCl and extracted with EtOAc. The organic portion was washed with brine (2×), dried ($MgSO_4$), filtered and concentrated in vacuo. FCC (silica gel, 100% EtOAc) gave 36.2 mg (72%) of the free acid 12 as a light yellow, viscous oil.

In an in-vitro assay for binding to and activity at prostaglandin receptors, the compound of Example 10 was shown to be selective at the EP2 and EP4 receptors as compared to the FP, EP1, TP, IP and DP receptors.

TABLE

| Compound | cAMP | bhEP$_2$ | fhEP$_2$ | bhEP$_4$ | fhEP$_4$ |
|---|---|---|---|---|---|
| 12 | 5560 | 248 | 50K | 15K | |

While particular embodiments of the invention have been described it will be understood of course that the invention is not limited thereto since many obvious modifications can be made and it is intended to include within this invention any such modifications as will fall within the scope of the appended claims.

The invention claimed is:

1. A method of providing neuroprotection to the eye of a mammal which comprises administering to the eye of said mammal a compound represented by the formula:

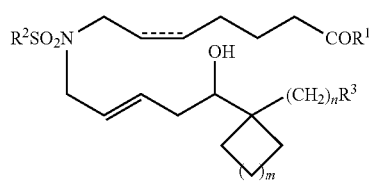

wherein $R^1$ is selected from the group consisting of $C_1$-$C_{10}$ alkoxy, OH and $NR^4R^5$;

$R^2$ is selected from the group consisting of $C_1$-$C_{10}$ alkyl and $(CH_2)_nOH$;

$R^3$ is selected from the group consisting of $C_1$-$C_{10}$ alkyl, phenyl, thienyl, furanyl, pyridyl and mono, -di-, tri-substituted phenyl, thienyl, furanyl and pyridyl;

$R^4$ and $R^5$ are independently selected from the group consisting of H, $C_1$-$C_{10}$ alkyl, $C_1$-$C_{10}$ alkyl hydroxyl;

m is 0 or an integer from 1 to 3 and n is an integer of from 1 to 4.

2. The method of claim 1 wherein $R^3$ is selected from the group consisting of thienyl, furanyl and pyridyl.

3. The method of claim 1 wherein $R^3$ is selected from the group consisting of $C_1$-$C_{10}$ alkyl.

4. The method of claim 1 wherein $R^1$ is OH or O-lower alkyl, wherein said lower alkyl is a $C_1$-$C_6$ alkyl.

5. The method of claim 1 wherein $R^1$ is selected from the group consisting of $N(H)_p$(lower alkyl)$_q$ or $N(H)_p$ (lower alkylhydroxyl)$_q$ wherein said lower alkyl is a $C_1$-$C_6$ alkyl.

6. The method of claim 1 wherein $R^2$ is a $C_1$-$C_6$ lower alkyl and the n associated with $R^2$ is 1.

7. The method of claim 1 wherein said compound is 7-[[5-Hydroxy-5-(1-propylcyclobutyl)pent-2-enyl]methanesulfonylamino]heptanoic acid ethyl ester).

8. The method of claim 1 wherein said compound is 7-[[5-Hydroxy-5-(1-propylcyclobutyl)pent-2-enyl]methanesulfonylamino]heptanoic acid.

9. The method of claim 1 which comprises administering an ophthalmic solution comprising a therapeutically-effective amount of the compound of claim 1 in ophthalmically-acceptable vehicle.

10. The method of claim 9 wherein said vehicle is saline.

11. The method of claim 10 wherein said solution comprises from 0.001-5% w/v of said compound.

12. A compound represented by the formula:

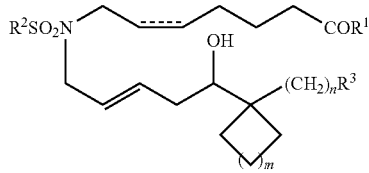

wherein $R^1$ is selected from the group consisting of $C_1$-$C_{10}$ alkoxy, OH and $NR^4R^5$;

$R^2$ is selected from the group consisting of $C_1$-$C_{10}$ alkyl and $(CH_2)_nOH$;

$R^3$ is selected from the group consisting of $C_1$-$C_{10}$ alkyl, phenyl, thienyl, furanyl, pyridyl and mono, -di-, tri-substituted phenyl, thienyl, furanyl and pyridyl;

$R^4$ and $R^5$ are independently selected from the group consisting of H, $C_1$-$C_{10}$ alkyl, $C_1$-$C_{10}$ alkyl hydroxyl;

m is 0 or an integer from 1 to 3 and n is an integer of from 1 to 4.

13. A method for treating ocular hypertension or glaucoma which comprises administering to a mammal having ocular hypertension a therapeutically effective amount of a compound of the formula

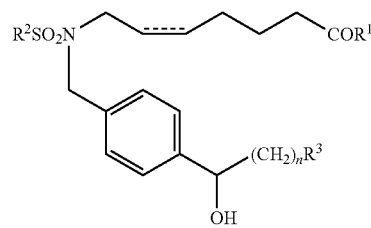

wherein $R^1$ is selected from the group consisting of $C_1$-$C_{10}$ alkoxy, OH and $NR^4R^5$;

$R^2$ is selected from the group consisting of $C_1$-$C_{10}$ alkyl and $(CH_2)_nOH$;

$R^3$ is selected from the group consisting of $C_1$-$C_{10}$ alkyl, thienyl, furanyl, pyridyl and mono, -di-, tri-substituted phenyl, thienyl, furanyl and pyridyl;

$R^4$ and $R^5$ are independently selected from the group consisting of H, $C_1$-$C_{10}$ alkyl, $C_1$-$C_{10}$ alkyl hydroxyl and n is 0 or 1.

\* \* \* \* \*